| United States Patent [19] | [11] Patent Number: 5,064,723 |
| --- | --- |
| Lawson | [45] Date of Patent: Nov. 12, 1991 |

[54] METAL TREATMENT

[75] Inventor: John R. Lawson, Manchester, England

[73] Assignee: Imperial Chemical Industries PLC, London, England

[21] Appl. No.: 652,206

[22] Filed: Feb. 5, 1991

Related U.S. Application Data

[63] Continuation of Ser. No. 436,102, Nov. 13, 1989, abandoned, which is a continuation of Ser. No. 169,571, Mar. 17, 1988, abandoned.

[30] Foreign Application Priority Data

Apr. 1, 1987 [GB] United Kingdom ............... 8707799

[51] Int. Cl.$^5$ ............................................. B32B 9/00
[52] U.S. Cl. ................................... 428/457; 156/330; 428/195; 428/209; 428/447; 428/470; 428/901; 428/459; 428/478.2
[58] Field of Search ............... 156/330; 428/195, 209, 428/447, 457, 420, 901, 459, 478.2

[56] References Cited

U.S. PATENT DOCUMENTS

| 3,837,964 | 9/1974 | Cotton et al. | 428/470 |
| 4,428,987 | 1/1984 | Bell et al. | 156/330 |
| 4,448,847 | 5/1984 | Bell et al. | 428/457 |
| 4,636,441 | 1/1987 | Sarinyan et al. | 428/447 |

FOREIGN PATENT DOCUMENTS

A0069937  7/1982  European Pat. Off. .

OTHER PUBLICATIONS

Chemical Abstracts, vol. 94, No. 15, Apr. 13, 1981, p. 658, ref. No. 121108r.
Chemical Abstracts, vol. 68, No. 7, Feb. 12, 1968, p. 2925, ref. No. 29995t.
Y. Kanoka et al., Chem. Pharm. Bull. (Tokyo) 15(11), 1738–43 (1967).
Chemical Abstracts, vol. 69, No. 17, Oct. 21, 1968, p. 6295, ref. No. 6737op.
Chemical Abstracts, vol. 81, No. 25, Dec. 23, 1974, p. 543, ref. No. 169485v.

*Primary Examiner*—Patrick J. Ryan
*Assistant Examiner*—Elizabeth Evans
*Attorney, Agent, or Firm*—Cushman, Darby & Cushman

[57] ABSTRACT

A compound containing a ligand group and a group of the general formula $-NRCOR^1{}_aX_bCR^2=CHCOR^3$ is used for treatment of a metal. The ligand group can be a triazole, an imidazole, an indazole, a thiazole, an oxazole, a carbamate, an xanthate or a phthalazine, or derivatives thereof. The compounds can be coated onto a metal surface, for example a copper surface. The metal surface may also be coated, simultaneously or subsequently, with a surface coating composition such as a paint or lacquer or an adhesive. When used with an adhesive, an increase in the adhesive strength is achieved.

20 Claims, No Drawings

METAL TREATMENT

This is a continuation of application Ser. No. 07/436,102, filed on Nov. 13, 1989, abandoned, which is a continuation of application Ser. No. 07/169,571, filed Mar. 17, 1988, abandoned.

The present invention relates to the treatment of metals and, in particular, to such a treatment to provide improved bonding of coating compositions applied to the surface.

It is known to apply a coating to a metal surface to improve the adhesion of a surface composition which is also applied to the metal surface. In particular, it is known to apply a coating to a metal surface which improves the strength of an adhesive bond when an adhesive composition is applied to the coated metal surface. Compounds which can be used to give improved adhesion are typically called adhesion promoters. Such compounds can be used to improve bonding in production of composite articles or in the production of printed circuit boards. An effective class of adhesion promoter for bonding of copper substrates is disclosed in U.S. Pat. No. 3,837,964. Other adhesion promoters are disclosed in U.S. Pat. Nos. 4,428,987 and 4,448,847. Organosilanes can be used as adhesion promoters, such as, for example gamma-glycidoxypropyltrimethoxysilane and other silanes containing a functional substituent. We have now found a further class of compounds which are effective as adhesion promoters.

According to the present invention there is provided a process which comprises coating a metal surface with a compound containing a ligand group and a group of the formula:

$$-NRCOR^1{}_aX_bCR^2=CHCOR^3$$

or a salt of said compound, wherein:
R is a hydrogen atom or a monovalent hydrocarbyl or substituted hydrocarbyl group;
$R^1$ is a divalent hydrocarbyl or substituted hydrocarbyl group;
$R^2$ is a hydrogen atom or an alkyl group;
$R^3$ is a group —OR or —$NR_2$, wherein the groups R in the —$NR_2$ group may be the same or different;
X is a divalent group —NRO— or —NRCO—;
a is zero or one; and
b is zero or one.

The ligand group preferably contains at least two hetero-atoms, by which is meant an atom other than carbon or hydrogen. The hetero-atom can be, for example, a nitrogen, sulphur or oxygen atom. Many suitable ligand groups contain at least one of the hetero-atoms in a ring system. The ligand group may be a triazole, an imidazole, an indazole, a thiazole, an oxazole, a carbamate, a xanthate or a phthalazine group or a derivative thereof. Derivatives of the ligand group include benzotriazole, naphthotriazole, benzimidazole, naphthimidazole, 2-mercaptothiazole, 2-mercaptobenzothiazole, 2-mercaptobenzimidazole, 2-mercaptobenzoxazole and carbamate derivatives such as dithiocarbamates.

For convenience hereafter, the group of the formula —$NRCOR^1{}_zX_bCR^2=CHCOR^3$ will be referred to as the "unsaturated amido group". It will be appreciated that the unsaturated amido group is separate from the ligand group and together the two groups form the compounds which are used in the process of the present invention. The unsaturated amido group may be bonded to one of the hetero-atoms of the ligand group, but is preferably bonded to a carbon atom of the ligand group. Preferred compounds for use in the process of the present invention are those in which the ligand group is a part of a fused ring system, for example as in benzotriazole, and the unsaturated amido group is bonded to one of the carbon atoms of the benzo group, for example as in a 5-substituted benzotriazole or a 4-substituted naphthotriazole.

In the unsaturated amido group, the group R attached to the nitrogen atom is preferably hydrogen but may be a lower alkyl group, that is an alkyl group containing 1 to 4 carbon atoms, particularly a methyl group. The group $R^1$ is typically an alkylene group, particularly a straight chain alkylene group. Thus, the group $R^1$ can be a group of the type —$(CH_2)_n$— where n is an integer. The value of n is typically at least 2, and particularly is at least 4. In general, no particular benefit is gained if the value of n is in excess of 30 and generally satisfactory compounds are those in which the value of n does not exceed 20. In the group X, the group R is typically a hydrogen atom but may be a lower alkyl group. It is preferred that a and b are both zero or are both one. The group $R^2$ is conveniently a hydrogen atom but may be a lower alkyl group such as a methyl group. The group $R^3$ can be a group —OH or a group —$NH_2$. If the group $R^3$ is a group —OH, the hydrogen can be replaced by a cation, for example an alkali metal such as sodium, to form a salt. Alternatively, $R^3$ may be a hydrocarbonoxy group or a substituted amino group but it is generally preferred that $R^3$ is a group —OH or a salt derived from the group —OH by replacing the hydrogen by a cation. The group —$COR^3$ may be in the cis- or trans- position with respect to the group —NRCOR$^1{}_aX_b$—. However, as discussed in more detail hereafter, the compounds of the present invention are conveniently prepared using maleic anhydride and hence the group —$COR^3$ is typically in the cis- position with respect to the group —NRCOR$^1{}_aX_b$—.

In one class of compound for use in the process of the present invention, the ligand group is benzotriazole and the unsaturated amido group is in the 5 position. In one compound of this type, the group R is a hydrogen atom, a and b are both zero, $R^2$ is a hydrogen atom and $R^3$ is a group —OH, this compound being 5-(3'-carboxyacryloylamino)benzotriazole. A preferred compound of this type is one in which R is a hydrogen atom, a and b are both one, $R^1$ is a tetramethylene, pentamethylene or undecamethylene group, X is —NHCO—, $R^2$ is a hydrogen atome and $R^3$ is a group —OH, such as, for example 5-[6'-(3''-carboxyacryloylamino)hexanoylamino]benzotriazole. In an alternative class of compound, the ligand group is benzothiazole or substituted benzothiazole as in 6-(3'-carboxyacryloylamino)-2-mercaptobenzthiazole.

The compounds to be used in the process of the present invention may be prepared by the application of known reaction conditions. A particularly convenient process is by the reaction of maleic anhydride, or a substituted derivative thereof, with an amino-substituted derivative of the ligand group, for example by the reaction of maleic anhydride with 5-aminobenzotriazole or 5-(6'-aminohexanoylamino)benzotriazole. The reaction between the anhydride and the amino compound is preferably effected in a solution in a polar solvent such as acetic acid or aqueous acetone. The reaction temperature generally does not exceed 100° C., and preferably does not exceed 50° C. and may conveniently be ambient temperature. The produce typically is precipitated and can be isolated by filtration. The product may be purified by dissolution in water at a high pH of at least 7, which is preferably at least 10, followed by acidification to a pH of less than 7 and filtration of the solid precipitated.

In accordance with the process of the present invention, the compounds can be coated onto metal surfaces and such a treatment is effective to increase the bond strength between the metal and a surface coating applied to the metal.

Thus as a further aspect of the present invention, there is provided a process which comprises coating a metal surface with a compound which is a 5-substituted benzotriazole or a 6-substituted-2-mercaptobenzothiazole where the substituent group is an unsaturated amido group as herein defined.

The metal surface may also be coated with a coating composition. The coating composition may be any known coating composition of a type which can be applied to a metal surface. The coating composition may be an adhesive composition such as, for example an epoxy or acrylic adhesive. The adhesive composition may be any adhesive composition which has previously been proposed for bonding onto metal surfaces, for example a partially pre-polymerised adhesive. The adhesive may be a highly functionalised, low-molecular weight adhesive, for example a low molecular weight acrylic adhesive or a B-stage epoxy adhesive.

Typically the adhesive is only partially polymerised and curing of the adhesive is effected after it has been coated onto the metal surface. Depending on the particular adhesive used, it may be necessary to incorporate a curing agent into the adhesive either before, during or after coating of the adhesive onto the metal surface. Curing of the adhesive is effected under the appropriate conditions for the particular adhesive. The process of the present invention can be used when coating a metal with an adhesive which can be cured at about ambient temperature, for example from 15° C. to 30° C. and a moderate applied pressure, for example from 100 kNm$^{-2}$ to 10 MNm$^{-2}$, such conditions typically being used for cold cure acrylic adhesives. The process of the present invention can also be used with an adhesive which is cured at an elevated temperature which is typically at least 100° C., particularly at least 150° C., for example about 180° C., using an applied pressure which is typically in the range 100 kNm$^{-2}$ to 10 MNm$^{-2}$, such conditions commonly being used with hot cure epoxy adhesives.

In accordance with the further aspect of the present invention, two metal surfaces may be coated with the compound of the type defined herein and also with an adhesive, and the metals are then bonded together by pressing the surfaces together under conditions effective to cause curing of the adhesive. The process of the further aspect of the present invention may be used to bond a metal to a non-metallic substrate, particularly a substrate formed from a plastics material such as a glass cloth impregnated with a partially cured epoxy resin or a fully cured epoxy resin-glass fibre board.

The process of the present invention can be used for coating of a metal surface. The metal may be an alloy and may be in strip, sheet, wire, powder or massive form. The metal may be copper, cobalt, zinc, nickel, silver or cadmium and is preferably copper. The metal surface which is to be coated is preferably brightly polished and/or freshly cleaned in order to maximize the desired effect.

A compound containing a ligand group and an unsaturated amido group, or the salt of such a compound, will hereafter be referred to simply as the "ligand compound".

The coating of the metal surface with a ligand compound may be effected by applying the ligand compound alone to the surface of the metal. However, it is generally preferred that coating is effected by applying the ligand compound in a suitable medium to the metal surface. More specifically, the ligand compound can be applied to the metal surface in the form of a solution in a suitable organic solvent, as a solution in an aqueous alkaline medium, when the ligand compound is believed to form a salt, as an aqueous emulsion of the ligand compound, or as an aqueous emulsion of a solution of the ligand compound in a suitable organic solvent. The coating of the metal surface with the ligand compound may be effected before the application of the coating composition. Alternatively, the ligand compound may be incorporated into the coating composition and the mixture thereof applied to the metal surface.

Conventional organic solvents may be used for the ligand compound and include for example alcohols, ethers, ketones and mixtures of these with aliphatic or aromatic hydrocarbons or with amides such as N,N-dimethylformamide. Especially preferred solvents are those having good wetting and drying properties and include for example ethanol, isopropanol and methylethylketone.

Aqueous emulsions of the ligand compound may be formed in conventional manner using conventional dispersants and surfactants, including non-ionic dispersants. It may be convenient to contact the metal surface with an aqueous solution or emulsion of a salt of the ligand compound or of the ligand compound.

If the ligand compound is coated onto the metal surface before applying the coating composition, the process of coating with the ligand compound may be repeated, if desired several times, before applying the coating composition. However, a single coating step gives generally useful results and hence the use of a single coating step is generally preferred.

Alternatively, the ligand compound may be formulated in the coating composition. As noted previously herein, the coating composition can be any known type of coating composition and we have obtained useful results using adhesive compositions. Other coating compositions which may be used include a paint (primer) such as an air-drying, oil-modified system or a system including a chlorinated rubber; a lacquer; a resin or other protective coating. The coating composition may be a solvent-based composition, for example a cellulose/solvent based primer paint such as those used for car "touch up" paints. The ligand compound is soluble in solvents generally used for such primers (for example nitrocellulose) and may be incorporated directly. The ligand compound may also be used as an emulsion in aqueous emulsion surface coating systems, for example primers or protective coatings based on polymer lattices such as for example acrylic and styrene/acrylic lattices and vinyl acrylic co-polymer lattices including acrylate modified vinyl chloride-vinylidene chloride copolymer lattices.

The ligand compound or the solution or emulsion thereof, may be applied to the metal in conventional manner, for example by dipping, spraying or brushing.

The temperature of the application may be from 0° to 60° C. Typically, solutions of the ligand compound may contain from 0.01 to 20% by weight of ligand compound, preferably from 0.01 to 5% by weight of the ligand compound. The presence of from 0.01 to 2% by weight of the ligand compound in a surface coating emulsion formulation is generally sufficient to provide improved adhesion of the surface coating and optimum effects have been obtained when applying, with a brush, a coating composition containing from 0.05 to 0.2% by weight of the ligand compound.

The process of the present invention may be used to bond a metal to a plastic or to bond together two sheets of metal. We have found that the adhesive strength of the bond formed is generally appreciably greater than the adhesive strength when using the adhesive alone. Failure of the bond is mainly cohesive rather than adhesive, hence failure is occurring within the adhesive rather than at the interface between the metal surface and the adhesive.

The present invention also provides a metal at least part of one surface of which has been coated with a ligand compound as hereinbefore defined.

The present invention further provides a metal at least part of one surface of which has been coated with a ligand compound as hereinbefore defined and also with a coating composition.

The ligand compound can be as previously described. The coating composition is preferably an adhesive composition.

The present invention also includes an article having a metal to metal bond wherein the metal surfaces bonded together have been treated with the ligand compound and with an adhesive.

Alternatively, the present invention includes an article having a metal to polymer bond wherein at least the metal surface has been treated with the ligand compound and with an adhesive.

The present invention may be applied to the production of a composite article having a metal to polymer bond or may be used for the production of articles wherein a metal is bonded to the same or a different metal using an adhesive.

The process of the present invention to produce a composite article having a metal to polymer bond may be used in the primary production of printed circuit boards (single, double sided or flexible boards) and elaboration of circuit boards (multilayer board fabrication, solder masks, photoresists and covercoats).

In accordance with a further aspect of the present invention, certain of the ligand compounds are new.

Thus, in accordance with this further aspect of the present invention there is provided a compound containing a ligand group and a group of the formula:

$$-NRCOR^1_aX_bCR^2=CHCOR^3$$

or a salt of said compound wherein:

R is a hydrogen atom or a monovalent hydrocarbyl or substituted hydrocarbyl group;
$R^1$ is a divalent hydrocarbyl or substituted hydrocarbyl group;
$R^2$ is a hydrogen atom or an alkyl group;
$R^3$ is a group —OR or —NR$_2$, wherein the groups R in the —NR$_2$ group may be the same or different;
X is a divalent group —NRO— or —NRCO—;
a is zero or one; and
b is zero or one;

with the proviso that when R and $R^2$ are hydrogen, $R^3$ is a group —OH, X is —NHCO—, and a and b are both one; the group $R^1$ is other than a pentamethylene group.

More specifically, this further aspect of the present invention provides, as new compounds, 5-(3'-carboxyacryloylamino)benzotriazole and 6-(3'-carboxyacryloylamino)-2-mercaptobenzothiazole.

Various embodiments of the present invention are set out in more detail in the following, non-limiting, examples. In the examples, unless stated to the contrary, parts are by weight with the exception of solvents where parts are by volume.

Preparation of
5-[6'-(3"-carboxyacryloylamino)hexanoylamino)benzotriazole 21.2 parts of 5-(6'-aminohexanoylamino)benzotriazole, which had been prepared as described in U.S. Pat. No. 3,837,964, were stirred with 100 parts of glacial acetic acid and warmed gently to about 40° C. in order to effect complete solution. The solution was cooled to 20° C. and 10 parts of maleic anhydride were added all at once. The mixture was stirred at ambient temperature for four hours. A pale cream precipitate was formed and this product was separated by filtration, washed with 30 parts of glacial acetic acid and then with 30 parts of methanol. The solid collected was then stirred in 100 parts of cold water and the pH of the suspension was adjusted to 12±0.5 by the addition of 13 parts of 10N aqueous sodium hydroxide solution. The resultant solution was stirred for one hour at 20° C., then acidified with 10 parts of glacial acetic acid, reducing the pH to 6±0.5. The resultant white suspension was filtered, washed well with cold water and dried in vacuo (20–25 mm mercury pressure) and 20° C. for 24 hours to yield 16.7 parts (55% yield) of the product, 5-[6'-(3"-carboxyacryloylamino) hexanoylamino]benzotriazole, m.pt. 182°–4° C. By analysis the product was found to contain C 52.4% wt; H 6.1% wt; and N 19.6% wt. A compound of the formula $C_{16}H_{19}N_5O_4.1.2H_2O$ requires C 52.5% wt; H 5.85% wt; and N 19.1% wt. For convenience hereafter, this product will be referred to as "CHB".

EXAMPLE 1

A mixture of 5.1 parts of 5-aminobenzotriazole, prepared as described in U.S. Pat. No. 4,428,987, 50 parts of water and 400 parts of acetone was warmed to 40° C. to effect a complete solution. To this solution was then added, all at once, a solution containing 5 parts of maleic anhydride dissolved is 25 parts of acetone. The resulting mixture was stirred at ambient temperature for four hours. A further charge of maleic anhydride (1.8 parts) was added, and stirring was continued at 20° C. for 16 hours.

The product (5.85 parts, 63% yield) was isolated by filtration, washed with acetone and dried in vacuo (20–25 mm mercury pressure) at 20° C. for 24 hours.

By analysis the product was found to contain C 48.9% wt; H 3.7% wt; and N 22.8% wt. The compound 5-(3'-carboxyacryloylamino)benzotriazole ($C_{10}H_8N_4O_3.0.75H_2O$) requires C 48.9% wt; H 3.9% wt; and N 22.8% wt.

EXAMPLE 2

(A) Preparation of 6-amino-2-mercaptobenzothiazole

A solution containing 100 parts of 2-mercaptobenzothiazole dissolved in 146 parts of concentrated sulphuric acid (SG 1.84) was cooled to 0°-2° C. This solution was treated with a mixture of 37 parts of fuming nitric acid (SG 1.5) and 30 parts of sulphuric acid (SG 1.84) over 3.5 hours, maintaining the internal temperature of the mixture at 0°-5° C. The mixture was allowed to warm to 20°-25° C. and stirred for a further 16 hours. The yellow solution was then poured carefully into 1000 parts of crushed ice which was being stirred. A pale yellow precipitate was formed which was isolated by filtration was washed well with cold water. The yellow filtercake was dissolved in 1000 parts of water and sufficient 10N aqueous sodium hydroxide solution to raise the pH of the solution to between 11 and 12. This solution was filtered and acidified, with stirring, to a pH in the range 2 to 3 by the addition of concentrated hydrochloric acid. A bright yellow precipitate (113 parts) was formed which was isolated by filtration and dried at 60° C. for 48 hours.

132 Parts of sodium hydrogen sulphide were dissolved in 400 parts of water, and stirred at 20° C. 53 Parts of 6-nitro-2-mercaptobenzothiazole, prepared as described previously herein, was added over 10 minutes; the reaction mixture was then heated to 110° C., and stirred whilst boiling the mixture under reflux conditions. After four hour boiling, the mixture was cooled to between 0° and 5° C. and stirred for one hour. The product, 6-amino-2-mercaptobenzothiazole, (30.3 parts) was isolated by filtration, washed sparingly with cold water and dried at 60° C. for 24 hours.

(B) Preparation of
6-(3'-carboxyacryloylamino)-2-mercaptobenzothiazole

A mixture containing 3.64 parts of 6-amino-2-mercaptobenzothiazole, prepared as described as described in part (A), and 600 parts of acetone was warmed to 40° C. to effect a complete solution. This solution was filtered, and treated with another solution containing 2.0 parts of maleic anhydride dissolved in 20 parts of acetone. The reaction mixture was stirred at ambient temperature. After about 0.5 hours, yellow crystals were observed in the solution. A further charge of maleic anhydride (1 part) was added after four hours, and stirring was continued for a further 16 hours.

The crystals (4.2 parts, 72% yield) were isolated by filtration, washed with acetone and dried in vacuo (20-25 mm mercury pressure) at 20° C. for 24 hours.

By analysis the product was found to contain C 45.2% wt; H 3.0% wt; N 9.6% wt; and S 22.4% wt. 6-(3'-carboxyacryloylamino)-2-mercaptobenzothiazole ($C_{11}H_8N_2O_3S_2.0.67H_2O$) requires C 45.2% wt; H 3.2% wt; N 9.6% wt; and S 22.0% wt.

EXAMPLE 3

Sheets of cooper foil, 0.1 mm in thickness and measuring 20×2 cms, where cleaned by light abrasion with a "Scotchbrite" pad, then immersed in 2N aqueous hydrochloric acid for 30 secons,d washed well with cold water, immersed in 2N aqueous sodium carbonate for 30 second, again washed well with cold water, then finally rinsed with ethanol and dried.

A sheet of copper foil treated as described was immersed in a solution containing 0.5 parts of the product of Example 1 dissolved in 10 parts dimethylformamide and 90 parts of industrial methylated spirits (hereafter "IMS") at 50° C. The foil was removed after 10 minutes immersion, washed with IMS and dried at 60° C. for 10 minutes. A laminate was prepared using the foil treated as described, an acrylic adhesive (Permabond F-245 - supplied by Permabond Adhesives Ltd., Woodside Road, Eastleigh, Hampshire, England) and a substrate which was fully cured epoxy-glass fibre board. The acrylic adhesive was cured at 20° to 25° C. under light pressure (2 kg.cm$^{-2}$) for 24 hours. The 90° peel strength of the laminate obtained, as measured using a laboratory Instron testing machine, and conditions as described in Ministry of Aviation test specification D.T.D.5577 was found to be 3.15 kNm$^{-1}$. A comparative laminate, prepared in a similar manner but excluding immersion of the copper foil in the solution containing the product of Example 1, was found to have a 90° peel strength, determined in the same manner, of 0.8 kNm$^{-1}$.

EXAMPLE 4

A sheet of copper foil which had been cleaned as described in Example 3, was immersed in a solution containing 0.5 parts of CHB in 10 parts of dimethylformamide and 90 parts of IMS at 50° C. After 10 minutes the foil was removed, washed with IMS and dried at 60° C. for 5 minutes.

A laminate was prepared from this copper foil using the procedure of Example 3. The laminate obtained had a 90° peel strength (determined as described in Example 3) of 2.1 kNm$^-$.

EXAMPLE 5

In an exactly analogous manner to that previously described in Examples 3 and 4, a strip of copper foil was pretreated with a solution containing 0.5 parts of the product of part (B) of Example 2 in 10 parts of dimethylformamide and 90 parts of IMS. A laminate was prepared from this foil as described in Example 3 and was found to have a 90° peel strength (determined as described in Example 3) of 1.8 kNm$^{-1}$.

EXAMPLE 6

A solution containing 0.1 parts of CHB in 5 parts of dimethylformamide and 95 parts of IMS was painted by brush directly onto the surface of a copper strip which had been cleaned as described in Example 3. After drying at 60° C. for 10 minutes, a laminate was prepared as described in Example 3. The 90° peel strength of this laminate (determined as described in Example 3) was 1.85 kNm$^{-1}$.

EXAMPLE 7

A copper strip, which had been cleaned as described in Example 3, was immersed in a solution containing 0.5 parts of the product of Example 1 in 100 parts of water at pH 9.5 and at 50° C. After 10 minutes the foil was removed, washed with cold water and dried at 60° C. for 5 minutes. A laminate was prepared from this foil as described in Example 3. The laminate obtained had a peel strength (determined as described in Example 3) of 1.4 kNm$^{-1}$.

EXAMPLE 8

A sheet of electrolytic copper foil, having one dendritic face, was cut into strips measuring approximately 20 cm×5 cm (this copper foil is typical of the material formed during the initial stages of the production of copper foil for use in printed circuit laminates). The strips were cleaned by immersion in aqueous 2N hydrochloric acid at 20° C. for 30 seconds, washed well with cold water (20° C.), immersed in 2N aqueous sodium carbonate at 20° C. for 30 seconds, again washed well with cold water, then finally rinsed with ethanol and dried in an oven at 50° C. for 5 minutes.

A strip of the copper foil treated as described was immersed in a solution containing 0.5 parts of the product of Example 1 dissolved in 10 parts of dimethylformamide and 90 parts of IMS at 50° C. After 30 minutes immersion, the foil was removed, washed with IMS and dried at 60° C. for 10 minutes.

A laminate was prepared by heating this copper foil with the dendritic face in contact with 10 layers of glass cloth impregnated with epoxy resin, (this material is of the type known in the trade as 'B-stage Epoxy Pre-Preg') for 20 minutes at 180° C. under a pressure of 2.07 $MNm^{-2}$ (300 p.s.i.). The 90° peel strength of the bond between the copper foil and the substrate, as measured on a laboratory Instron machine, was 1.4 $kNm^{-1}$. A further laminate was prepared from an untreated copper strip using the same procedure and was found to have a 90° peel strength of 1.1 $kNm^{-1}$.

COMPARATIVE EXAMPLE A

The procedure of Example 8 was repeated with the exception that the strip of copper foil was immersed in a solution containing 0.5 parts of the compound 5-(6-methacryloylamidohexanoylamido)-benzotriazole (prepared in accordance with the procedures described in U.S. Pat. No. 3,837,964) dissolved in 10 parts of dimethylformamide and 90 parts of IMS at 50° C. The 90° peel strength of the bond between the copper foil and the substrate, as measured on a laboratory Instron machine, was 0.86 $kNm^{-1}$. A similar laminate prepared from untreated copper was found to have a peel strength of 0.82 $kNm^{-1}$.

EXAMPLE 9

Sheet of electrolytic copper foil were cleaned as described in Example 8.

A strip of this foil, measuring 20 cm×5 cm, was painted with a solution containing 0.1 parts by weight of the product of Example 1 dissolved in 100 parts of a mixture of dimethylformamide (1 part) and IMS (99 parts). The foil so treated was dried in air at 60° C. for 5 minutes. A laminate was then prepared as described in Example 8. The average peel strength of the bond between the copper foil and substrate was 1.16 $kNm^{-1}$. By comparison, a laminate prepared from untreated copper foil was found to have a peel strength of 1.10 $kNm^{-2}$.

COMPARATIVE EXAMPLE B

The procedure described for Example 9 was repeated with the exception that the strip of copper foil was painted with a solution containing 0.1 parts of 5-(6-methacryloylamidohexanoylamido)-benzotriazole (as used in Comparative Example A) dissolved in 100 parts of IMS. The laminate produced had a peel strength of 0.63 $kNm^{-1}$. A similar laminate prepared from untreated copper foil was found to have a peel strength of 0.61 $kNm^{-1}$.

EXAMPLE 10

A sheet of rolled annealed copper foil, having one dendritic face, was cut into strips measuring approximately 20 cm×5 cm (this foil is typical of the material used in the production of printed circuit laminates). The foil was rinsed well with acetone and dried at 60° C. for 5 minutes.

A strip of the foil, cleaned as described, was sprayed on both sides with a solution containing 0.05 parts of the product of Example 1 dissolved in 10 parts of dimethylformamide and 90 parts of isopropanol. After drying at 60° C. for 10 minutes a laminate was prepared by heating the copper foil with the dendritic face in contact with 10 layers of B-stage Epoxy Pre-preg, as described in Example 8.

The peel strength of this laminate, as measured on a Tensometer 20 (Monsanto) machine, was 0.80 $kNm^{-1}$.

COMPARATIVE EXAMPLE C

A laminate was prepared by the procedure described of Example 10 with the exception that the copper strip was sprayed with 0.05 parts of 5-(6-methacryloylamidohexanoylamido)benzotriazole dissolved in 10 parts of dimethylformamide and 90 parts of isopropanol. The laminate obtained gave a peel strength of 0.73 $kNm^{-1}$.

For comparison with the laminates of Example 10 and Comparative Example C, a further laminate was prepared using the same procedure with an untreated strip of copper foil. The peel strength of this laminate was 0.71 $kNm^{-1}$.

I claim:

1. A metal having on at least part of one surface thereof, as an adhesion promoter, a coating of a compound containing a ligand group and a group of the formula:

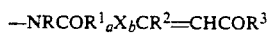

$$-NRCOR^1{}_aX_bCR^2\!=\!CHCOR^3$$

or a salt of said compound, wherein:
R is a hydrogen atom or a monovalent hydrocarbyl or substituted hydrocarbyl group;
$R^1$ is a divalent hydrocarbyl or substituted hydrocarbyl group;
$R^2$ is a hydrogen atom or an alkyl group;
$R^3$ is a group —OR or —$NR_2$, wherein the groups R is the —$NR_2$ group may be the same or different;
X is a divalent group —NRO— or —NRCO—;
a is zero or one; and
b is zero or one.

2. A printed circuit board comprising copper which is a coated metal as claimed in claim 1 and which is coated with a coating composition which is an adhesive composition and the copper is bonded to a plastics substrate.

3. The compound of claim 1 which is 5-(3'-carboxyacryloylamino)benzotriazole; or 6-(3'-carboxyacryloylamino)-2-mercaptobenzothiazole.

4. A coated metal as claimed in claim 1 wherein the compound is one in which the ligand group contains at least two heteroatoms.

5. A coated metal as claimed in claim 4 wherein the compound is one in which the group —NRCOR$^1{}_aX_bCR^2$=CHCOR$^3$ is bonded to a carbon atoms of the ligand group.

6. A coated metal as claimed in claim 1 wherein the compound is one in which $R^2$ is hydrogen and $R^3$ is a group —OH or a salt derived from the group —OH by replacing the hydrogen by a cation.

7. A coated metal as claimed in claim 1 wherein the compound is 5-(3-carboxyacryloylamino)benzotriazole; 5-[6'-(3''-carboxyacryloylamino)hexenoylamino]benzotriazole; or 6-(3'-carboxyacryloylamino)-2-mercaptobenzothiazole.

8. A coated metal as claimed in claim 1 wherein the metal surface is also coated with a coating composition which is an adhesive composition which is a partially pre-polymerized adhesive or a highly functionalized, low molecular weight adhesive.

9. A coated metal as claimed in claim 8 wherein the adhesive composition is a B-stage epoxy adhesive.

10. A compound containing a ligand group and a group of the formula:

—NRCOR$^1_a$X$_b$DR$^2$=CHCOR$^3$ or a salt of said compound, wherein the ligand group is selected from a carbanate, a xanthate, a phthalazine, a triazole, an imidazole, an indazole, a thiazole or an oxazole group or a derivative thereof and R is a hydrogen atom or a monovalent hydrocarbyl or substituted hydrocarbyl group;

R$^1$ is a divalent hydrocarbyl or substituted hydrocarbyl group;

R$^2$ is a group —OR or —NR$_2$, wherein the groups R in the —NR$_2$ group may be the same or different;

X is a divalent group —NRO— or —NRCO—;

a is zero or one; and b is zero or one, with the provisos that when R and R$^2$ are hydrogen, R$^3$ is a group —OH, X is —NHCO—, and a and b are both one; the group R$^1$ is other than a pentamethylene group; and when a and b are both zero, the ligand group is one in which the ligand group is a part of a fused ring system and the group —NRCOCR$^2$=CHCOR$^3$ is bonded to a carbon atom of the benzo group of the fused ring system.

11. A coated metal as claimed in claim 1 wherein the compound is one in which the ligand group is selected from a triazole, an imidazole, an indazole, a thiazole, an oxazole, a carbamate, a xanthate or a phthalazine group or a derivative thereof.

12. A coated metal as claimed in claim 11 wherein the compound is one in which the ligand group is part of a fused ring system.

13. A coated metal as claimed in claim 12 wherein the compound is one in which the group —NRCOR$^1_a$X$_b$CR$^2$=CHCOR$^3$ is bonded to a carbon atom of the benzo group of the fused ring system.

14. A coated metal as claimed in claim 1 wherein the compound is one is which the R$^1$ is a straight chain alkylene group.

15. A coated metal as claimed in claim 14 wherein the group R$^1$ is a group —(CH$_2$)$_n$— where n is an integer and has a value of at least 4.

16. A coated metal as claimed in claim 1 wherein the compound is one in which R is a hydrogen atom; a and b are both one; R$^1$ is a tetramethylene, pentamethylene or undercamethylene group; X is —NHCO—, R$^2$ is a hydrogen atom; and R$^3$ is a group —OH.

17. The compound of claim 10 wherein the ligand group is one in which a triazole, an imidazole, an indazole, a thiazole or an oxazole group is part of a fused ring system.

18. The compound of claim 17 wherein the group —NRCOR$^1_a$X$_b$CR$^2$=CHCOR$^3$ is bonded to a carbon atom of the benzo group of the fused ring system.

19. The compound of claim 18 wherein the ligand group is benzotriazole, benzothiazole or substituted benzothiazole.

20. The compound of claim 10 wherein the group R$^1$ is a group —(CH$_2$)$_n$—, where n is an integer and has a value of at least 2.

* * * * *